United States Patent [19]

Sakurai et al.

[11] Patent Number: 4,651,085
[45] Date of Patent: Mar. 17, 1987

[54] APPARATUS FOR MEASURING THE RATIO OF ALCOHOL CONTAINED IN MIXED FUEL

[75] Inventors: Takashi Sakurai; Hiroshi Mizuno, both of Nagoya; Yoshihisa Shibata, Kariya, all of Japan

[73] Assignee: Nippondenso Co., Ltd., Kariya, Japan

[21] Appl. No.: 597,097

[22] Filed: Apr. 5, 1984

[30] Foreign Application Priority Data

Apr. 6, 1983 [JP] Japan .................................. 58-60396
Apr. 14, 1983 [JP] Japan .................................. 58-65863
Apr. 20, 1983 [JP] Japan .................................. 58-69768

[51] Int. Cl.⁴ ...................... G01R 27/04; G01R 27/26
[52] U.S. Cl. ........................ 324/58.5 R; 324/58.5 A; 324/58.5 B; 324/58.5 C
[58] Field of Search ............... 324/61 R, 58 R, 58 A, 324/58 B, 58 C, 58.5 R, 58.5 A, 58.5 B, 58.5 C

[56] References Cited

U.S. PATENT DOCUMENTS

| | | | |
|---|---|---|---|
| 3,458,808 | 7/1969 | Agdur | 324/58.5 C |
| 3,498,112 | 3/1970 | Howard | 324/58.5 A |
| 3,612,996 | 10/1971 | Blackley | 324/58.5 A |
| 3,688,188 | 7/1972 | Bak | 324/58.5 C |
| 4,042,879 | 8/1977 | Ho | 324/58.5 C |
| 4,453,125 | 6/1984 | Kimura | 324/61 R |
| 4,490,676 | 12/1984 | Davis | 324/58.5 A |

FOREIGN PATENT DOCUMENTS 58-14144 1/1983 Japan .
1122987 8/1968 United Kingdom .......... 324/58.5 A Primary Examiner—Reinhard J. Eisenzopf
Assistant Examiner—Jose M. Solis
Attorney, Agent, or Firm—Cushman, Darby & Cushman

[57] ABSTRACT

An apparatus for measuring the ratio of alcohol contained in mixed fuel which flows through a fuel pipe to the engine. The fuel pipe is made of a high frequency signal permeable material such as rubber, teflon or nylon, for example. A microwave chamber is provided outside the fuel pipe, enclosing a part of the fuel pipe. The microwave chamber comprises a pair of wave guides opposed to each other with the fuel pipe interposed between them. One of the wave guides is provided with an antenna section for transmitting microwaves received from a microwave generator. The other wave guide is provided with a receiving antenna section for receiving the microwaves permeating through the fuel pipe through which the mixed fuel is flowing. The microwaves passing through the fuel pipe are attenuated according to the amount of alcohol in the fuel. The microwaves received by the antenna section are detected by a detector and converted to DC voltage signals which correspond to the strengths of the microwaves received and thus the amount of alcohol in the fuel.

20 Claims, 16 Drawing Figures

F I G. 1
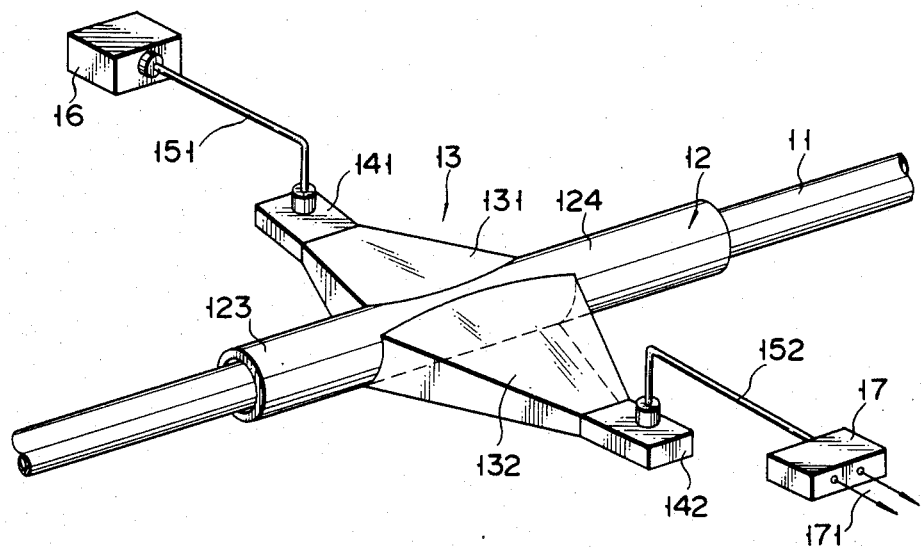
F I G. 2
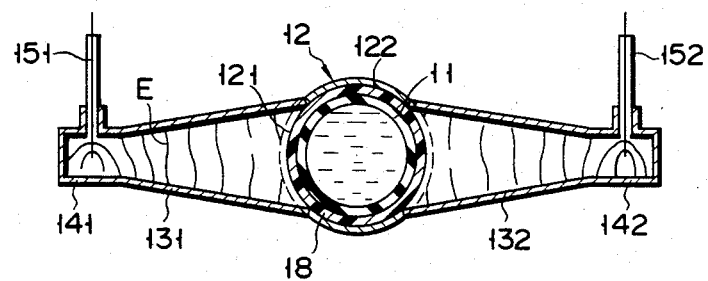

F I G. 9
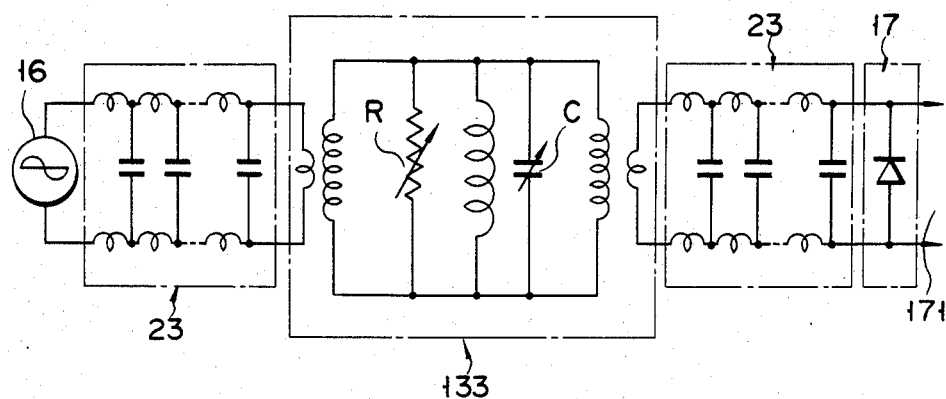
F I G. 10
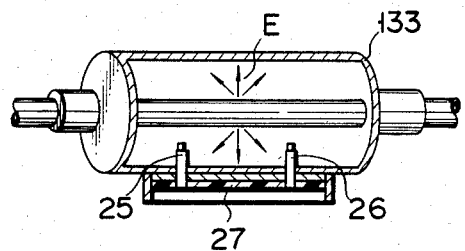
F I G. 11
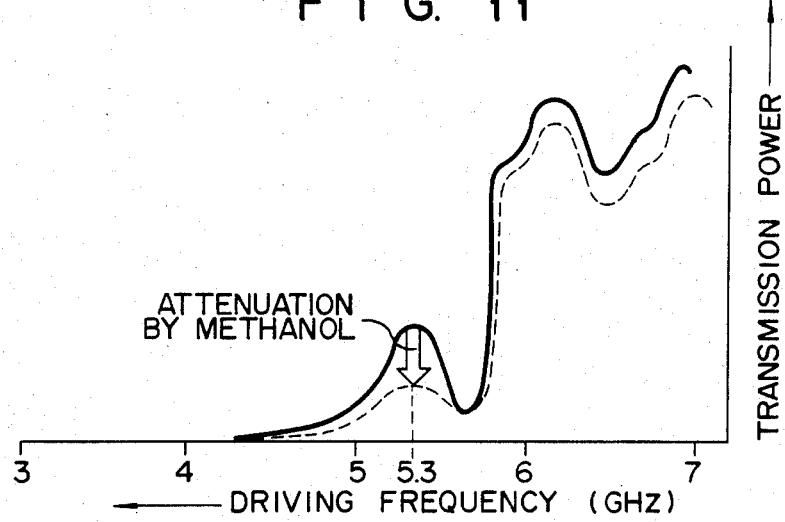

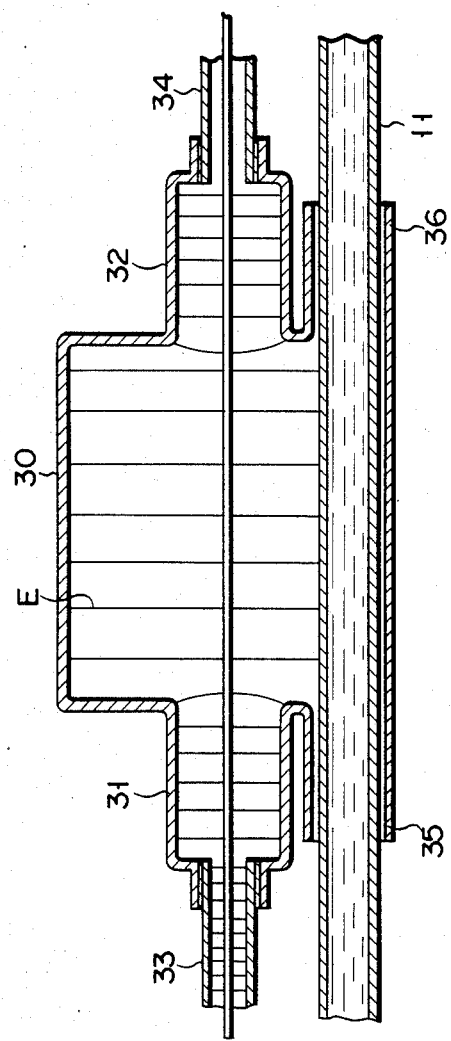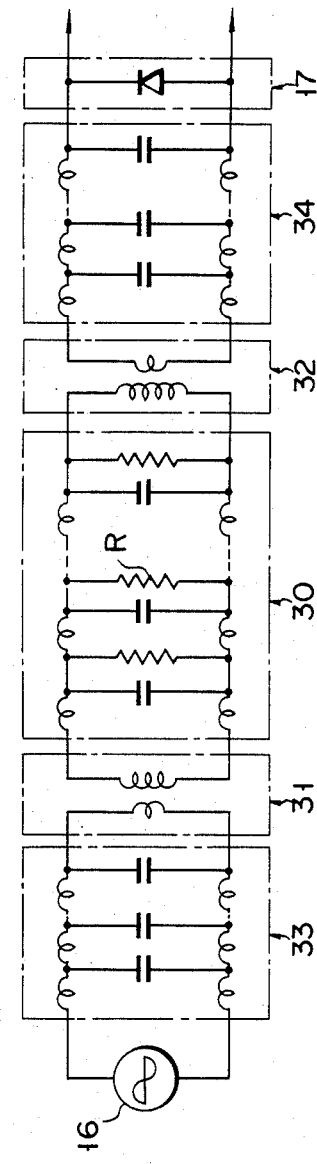
FIG. 14
FIG. 15

4,651,085

APPARATUS FOR MEASURING THE RATIO OF ALCOHOL CONTAINED IN MIXED FUEL

BACKGROUND OF THE INVENTION

The present invention relates to an apparatus for measuring the ratio of alcohol contained in mixed fuel, wherein the ratio of alcohol contained in fuel for use in a car engine, for example, is measured and used to achieve effective engine control in relation to the air/fuel ratio and the like.

Mixed fuels in which alcohol is mixed with gasoline or light oil have been used as car fuel, for example. In the case of using mixed fuels, it is necessary to accurately known the ratio of alcohol to gasoline or alcohol to light oil in order for the engine to be controlled in the most suitable way to achieve an efficient air/fuel ratio.

As an engine fuel, alcohol is different from gasoline in that it needs a different air/fuel ratio, different anti-knock components and so on. When alcohol-mixed fuel is used, but when electronic control of the engine is carried out according to an engine control program which uses only gasoline as fuel, the control output and vehicle driveability are lowered. This results in a violation of the exhaust gas pollution regulations. In the case of using mixed fuel, therefore, it is necessary to control the amount of fuel injected, the timing of the ignition and the like according to the ratio of alcohol contained in the mixed fuel. This is the reason why the ratio of alcohol contained in fuel must be accurately and easily detected and measured when mixed fuel is used.

The following are ways to measure the ratio of alcohol contained in mixed fuel. The first way is to use electrostatic capacity. A pair of electrodes are opposed to each other in a fuel pipe with a space between them in through which mixed fuel is passed. More specifically, the electrostatic capacity between the electrodes is measured based on the fact that the electrostatic capacity between the paired electrodes thus arranged will change depending upon the ratio of alcohol mixed into the fuel. The second way is to grasp, as impedance, the change in the electrostatic capacity between paired electrodes which have been arranged similar to those in the first method. The third is to arrange matter in the pipe, and then to detect and measure the ratio of alcohol contained, by measuring the change of in the matter's property caused by the interaction between the matter and alcohol particles.

When an alcohol ratio measuring device is to be provided according to any of these measures, it is necessary to arrange electrodes in the pipe through which fuel is supplied to the engine, thereby making that portion of the pipe where the electrodes are attached more complicated. It is necessary, particularly in this case, to prevent fuel leakage from that part of the pipe where the electrodes are attached. That part of the pipe must be made completely oil-tight and strong.

SUMMARY OF THE INVENTION

An object of the present invention is to provide an alcohol ratio measuring apparatus capable of measuring the amount of alcohol contained in mixed fuel from the outside of the pipe through which the mixed fuel is passed, without arranging any electrode in the mixed fuel, and of effectively picking up a detection signal used to control the operation of the engine control means, for example.

Another object of the present invention is to provide an alcohol ratio measuring apparatus which can be attached to the fuel pipe, without damaging the oil-tightness of the fuel pipe.

A further object of the present invention is to enable fuel, in which alcohol is mixed with gasoline or the like, to be effectively used in the car engine, and to enable the engine to be controlled in relation to the air/fuel ratio and the like under optimum conditions even when mixed fuel is used.

In the rubber hose which forms the pipe through which fuel is supplied to the engine, gasoline and light oil are almost transparent relative to an electromagentic wave while the electromagnetic wave absorption of the alcohol particles becomes extremely large in a band of microwaves frequencies varying from 1-10 GHz.

The present invention is derived from the fact that electromagnetic waves such as microwaves are extremely responsive to a dielectric which is present in the electromagnetic wave transmitting path. According to the present invention, the pipe through which the mixed fuel is passed is made of a material which allows microwaves to pass therethrough, a microwave chamber is attached to the outer circumference of the pipe, and a microwave signal is transmitted to and received from the microwave chamber, so that the ratio of alcohol contained can be measured and detected from the amount of attenuation at the time of microwave transmission and reception.

This alcohol ratio measuring apparatus can be attached to the outer circumference of the pipe without working or modifying the pipe, so that no influence acts on the fuel flowing in the pipe, and so that no fuel leakage is caused at that part of the pipe to which the device is attached. Accordingly, the alcohol ratio measuring apparatus can be attached, with safety, to the existing fuel pipe of a car engine, and the signal gained from the apparatus can be used, as it is, in a circuit for controlling the air/fuel ratio for the engine thereby enabling the engine, in which the mixed fuel is used to be controlled under the optimum conditions.

BRIEF DESCRIPTION OF THE DRAWINGS

FIG. 1 shows the configuration of a first embodiment of an alcohol ratio measuring apparatus according to the present invention;

FIG. 2 is a sectional view showing a microwave chamber of the apparatus shown in FIG. 1;

FIG. 9 is a diagram showing an equivalent circuit for the embodiment shown in FIG. 8;

FIG. 10 shows a fourth embodiment of the present invention, partly cut off;

FIG. 11 is a characteristic curve diagram showing the relationship between the driving frequency in the apparatus and the power transmitted through the methanol portion;

FIG. 14 is a sectional view showing a further microwave chamber of the apparatus shown in FIG. 13; and FIG. 15 shows an equivalent circuit for the fifth embodiment.

DETAILED DESCRIPTION OF THE PREFERRED EMBODIMENTS

Figure 3:
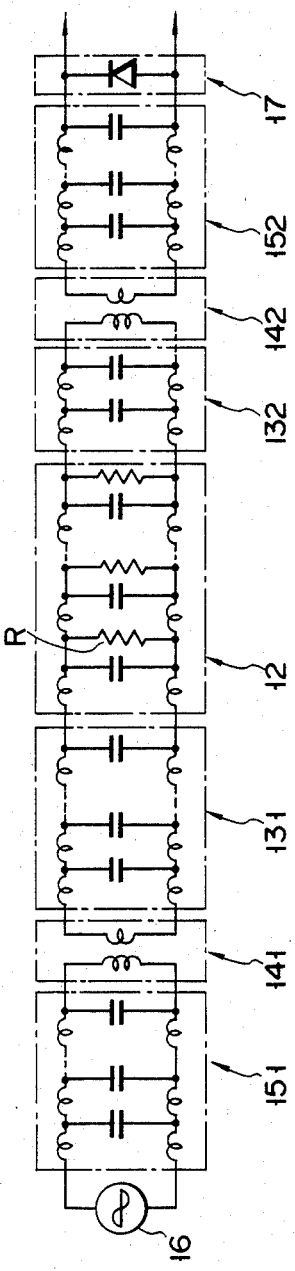
FIG. 3 is a diagram showing an equivalent circuit for the first embodiment.

FIGS. 1 and 2 shows the configuration of an apparatus for detecting and measuring the amount of alcohol contained in mixed fuel which is supplied to the engine. The mixed fuel (in which alcohol is mixed with gasoline, for example), is supplied to the engine (not shown) through a fuel pipe 11, which is made of a material such as rubber, teflon or nylon which allows high frequency signals to pass therethrough. That part of the pipe 11 where the ratio of alcohol contained in the passing fuel is to be determined is covered by a cylindrical metal member 12.

The cylindrical member 12 is provided with openings 121 and 122 which are opposite to each other. Fitted into the openings 121 and 122 are microwave wave guides 131 and 132 with the fuel pipe 11 interposed between them to form a microwave chamber 13. Each of the wave guides 131 and 132 is formed like a pyramid, taking the opening of the cylindrical member 12 as its bottom, and provided with an antenna section 141 or 142 as its top, to which a coaxial cable 151 or 152 is connected. A microwave signal is supplied from a microwave signal generator 16 to the coaxial cable 151 while a microwave detector 17 is connected to the coaxial cable 152. More specifically, a microwave signal generated from the generator 16 is introduced into the wave guide 131 through the coaxial cable 151 and the antenna section 141, is further guided from the wave guide 131 into the wave guide 132, passing through the pipe 11, and then is received at the antenna section 142 to be detected by the microwave detector 17 through the coaxial cable 152.

Interposed between the pipe 11 and the cylindrical member 12 is a cylindrical spacer 18, which is made of a high frequency permeable material similar to the pipe 11, to enable the cylindrical member 12 to be attached to the pipe 11 with solidness. The cylindrical member 12 is provided with extended portions 123 and 124 formed on both sides of the openings 121 and 122 which are opposed to the wave guides 131 and 132, respectively. Each of these extended portions 123 and 124 is made long enough to set the cut-off frequency at each of these portions to be sufficiently higher than the signal frequency generated from the microwave generator 16 which is used to measure the ratio of alcohol contained. Namely, these extended portions serve to prevent microwaves from leaking outside through both end portions of the cylindrical member 12.

The microwaves supplied from the generator 16 to the antenna section 141 through the coaxial cable 151 are transmitted to the wave guide 131 of the microwave chamber 13, are transmitted through the wave guide 131, generating the wave field shown by E in FIG. 2, and are further transmitted into the wave guide 132, passing through the pipe 11. The microwaves transmitted to the wave guide 132 are received at the antenna section 142 and then are detected by the detector 17 through the coaxial cable 152. The detector 17 generates a DC voltage signal whose amplitude is proportional to that of the microwaves received. This voltage signal is supplied, as one of the control signals, to the air/fuel ratio control means (not shown) for the engine through lead lines 171.

The electromagnetic wave which accompanies the wave field E of the microwave signal attenuates when it passes through a dielectric in such a way that it is proportional to a dielectric loss factor $\epsilon \tan \delta$ which is the product of the dielectric constant $\epsilon$ and the dielectric loss tangent $\tan \delta$ of the dielectric. Table 1 shows the relationship between the dielectric constant $\epsilon$ and the dielectric loss tangent $\tan \delta$ as it relates to methanol, gasoline, teflon and nylon.

TABLE 1

| Dielectric | $\epsilon$ | $\tan \delta$ |
|---|---|---|
| methanol | 24 | 6400 |
| gasoline | 2 | 14 |
| teflon | 2 | 1.5 |
| nylon | 3 | 130 |

As apparent from Table 1, methanol is the largest both in the dielectric constant $\epsilon$ and the dielectric loss tangent $\delta$. In mixed fuel in which methanol, for example, has been mixed with gasoline, therefore, the dielectric loss factor $\epsilon \tan \delta$ of this mixed fuel becomes larger, corresponding to the increase in the amount of methanol mixed.

When the mixed fuel is passed through a fuel pipe 11 made of teflon or nylon whose dielectric loss factor $\epsilon \tan \delta$ is small, therefore, microwaves passing from the wave guide 131 to the other wave guide 132 are attenuated not by the pipe but by the amount of methanol mixed in the mixed fuel in the pipe 11. The attenuated microwaves are then transmitted to the wave guide 132.

Microwaves propagating through air in the wave guide 131, whose dielectric constant $\epsilon$ is small, are reflected by the fuel in the fuel pipe 11, whose dielectric constant $\epsilon$ is large. This reflection becomes more severe as the dielectric constant $\epsilon$ of the fuel or the amount of methanol mixed in the fuel becomes larger. Thus, the microwaves transmitted to the wave guide 132, show a similar attenuation. Accordingly, the amount of methanol mixed in the mixed fuel in the pipe can be found by measuring the level of the microwave signals which have reached the detector 17 and by detecting the amount of attenuation in the microwave.

The above-described alcohol ratio measuring device makes the devices unnecessary for it to be arranged within the pipe in which mixed fuel is present, thereby preventing fuel leakage and enabling maintenance to be easily performed. In addition, current wasted by the device is only about 2W, which is no burden upon the battery power source mounted in the car.

Figure 4:
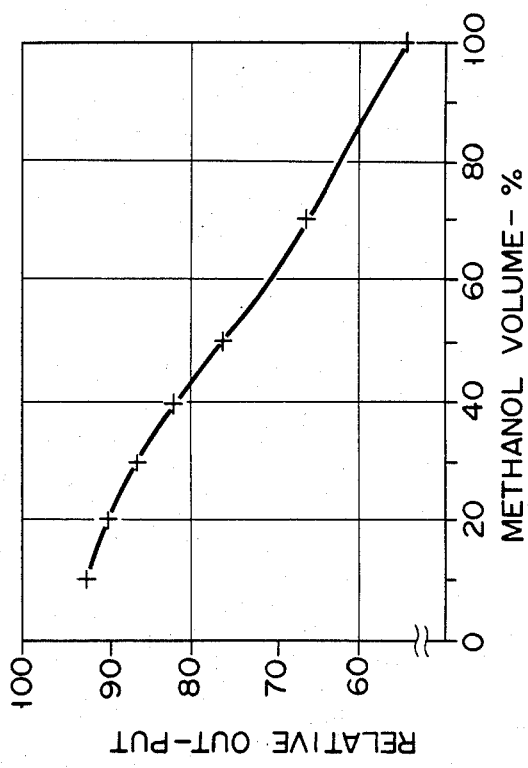
FIG. 4 is a curve showing the relationship between the relative output of the apparatus and the methanol contained inside.

FIG. 3 shows an equivalent circuit for the apparatus, in which the dielectric loss factor $\epsilon \tan \delta$ of mixed fuel in the fuel pipe 11 is denoted by the distributing resistance R. FIG. 4 shows the relative output of the alcohol ratio measuring apparatus in relation to methanol volume percentage.

Figure 5:
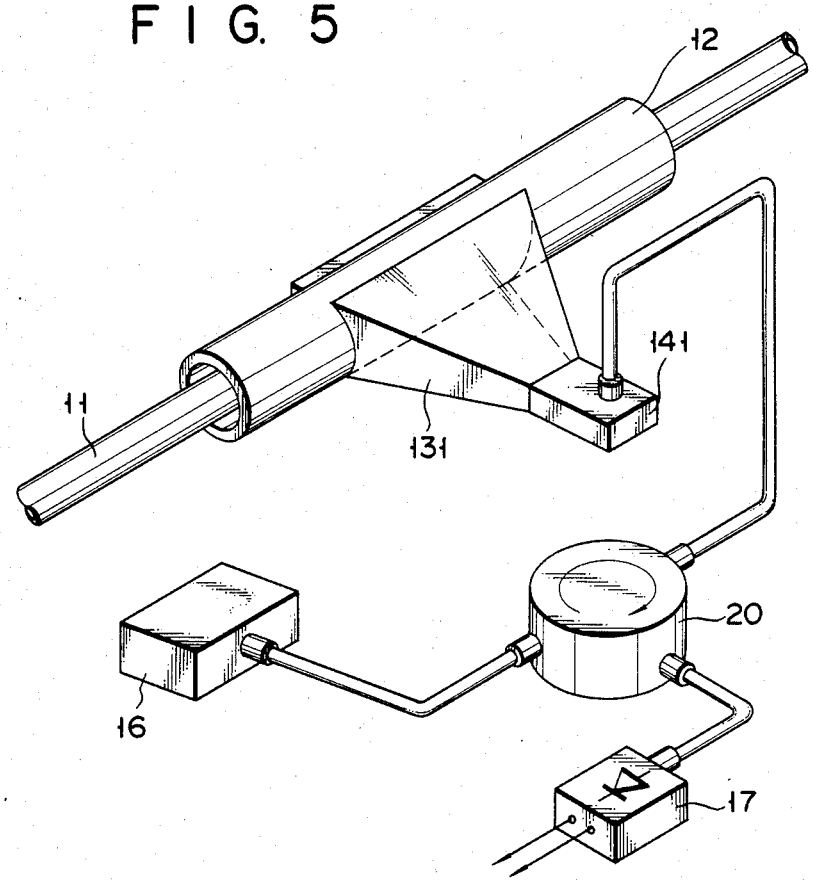
FIG. 5 shows the configuration of a second embodiment according to the present invention.
Figure 6:
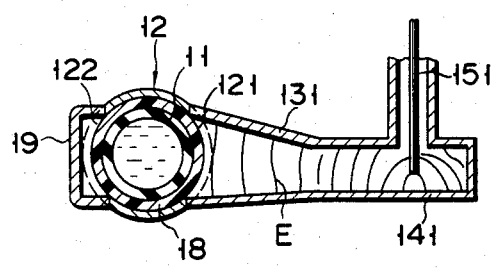
FIG. 6 is a sectional view showing another microwave chamber of the apparatus shown in FIG. 5.

FIGS. 5 and 6 show a second embodiment of the present invention in which the wave guide 132 of the first embodiment shown in FIGS. 1 and 2 is omitted. A reflecting plate 19 is attached to the opening 122 of the cylindrical member 12, instead of the wave guide 132, to thereby close the opening 122. Microwaves generated by the antenna section 141 in the wave guide 131 pass through the pipe 11, are reflected by the reflecting plate 19, and pass through the pipe 11 again to return to the wave guide 131. The microwaves thus reflected are received at the antenna section 141. A coaxial cable 151 extending from the antenna section 141 is connected to the generator 16 and the detector 17 via a circulator 20. Namely, microwaves are guided from the generator 16 to the wave guide 131 through the circulator 20 and the coaxial cable 151, while they are guided from the wave guide 131 to the detector 17 through the coaxial cable 151 and the circulator 20.

Figure 7:
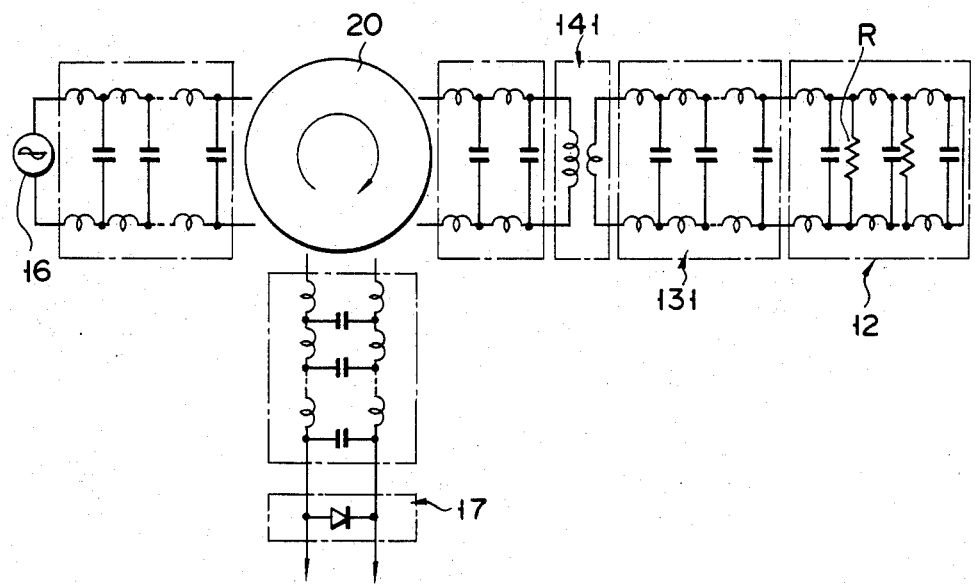
FIG. 7 is a diagram showing an equivalent circuit for the second embodiment.

FIG. 7 shows an equivalent circuit for the second embodiment of the present invention.

In the case of the second embodiment, the reflected wave which has been attenuated after passing through the fuel is picked up directly by the circulator 20 to measure the microwave strength, but its magnitude may be indirectly measured from the magnitude of the standing wave which is composed of the progressive and reflected waves in the wave guide.

Also in the second embodiment, the microwave chamber 13 can be formed by a wave guide. However, it may also be formed by a microwave resonance chamber.

Figure 8:
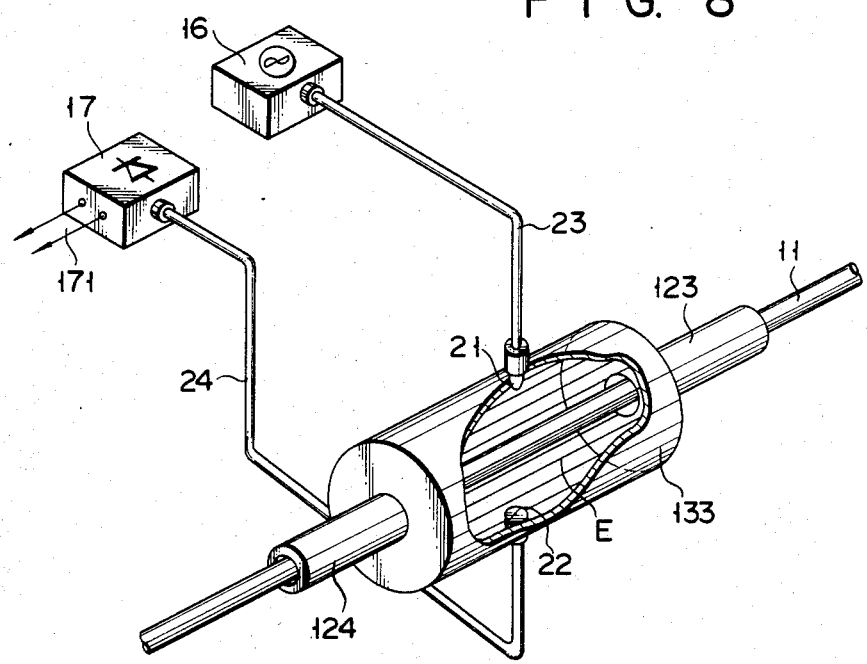
FIG. 8 shows a third embodiment of the present invention, partly cut off.

FIG. 8 shows a third embodiment of the present invention, in which a cylindrical microwave resonance chamber 133 is arranged around the fuel pipe 11. The resonance chamber 133 is supported by cylindrical members 123 and 124 which are made of metal. A spacer is interposed between the cylindrical member 123 or 124 and the pipe 11 to stably hold the resonance chamber 133 around the pipe 11. Arranged on both sides of the cylindrical resonance chamber 133 are transmitting and receiving loop antennas 21 and 22, which are connected to the microwave generator 16 and the detector 17 through coaxial cables 23 and 24, respectively.

A microwave signal generated by the generator 16 is transmitted from the antenna 21 to the resonance chamber 133, where it is resonated and amplified. When the dielectric loss factor $\epsilon \tan \delta$ of fuel in the pipe 11 located in the resonance chamber 133 is small, the microwaves introduced into the resonance chamber 133 are resonated and amplified effectively, without being reflected and attenuated, and are then received by the receiving antenna 22. When the amount of alcohol mixed with gasoline increases in the pipe 11, however, the dielectric constant $\epsilon$ of this mixed fuel becomes large, the microwave is caused to reflect in the resonance chamber 133, and the resonance frequency in the resonance chamber 133 is shifted to quickly lower the strength of this microwave. The dielectric loss factor $\epsilon \tan \delta$ of the mixed fuel also becomes large at the same time the resonance microwave is attenuated, so that the strength of the microwave received by the receiving antenna 22 can be attenuated and set depending upon the amount of alcohol contained in the mixed fuel in the pipe 11.

FIG. 9 shows an equivalent circuit for the third embodiment, in which the shift of the resonance frequency in the hollow resonance chamber 133 (which frequency shift depends upon changes in dielectric constant $\epsilon$ of the mixed fuel as it passed through the fuel pipe 11) is represented by a variable capacitor C, and in which the attenuation of the resonance microwave (which attenuation depends upon the dielectric loss factor $\epsilon \tan \delta$ of the mixed fuel) is represented by a resistance R.

When the pipe 11 is a rubber hose in the above-described third embodiment, the resonance frequency characteristic is largely influenced by the pipe 11. Why is this influence caused by the rubber hose which is permeable to electromagnetic waves? It has been found that if a large amount of carbon black which absorbs the electronic wave is added to the rubber of which the pipe is made, this carbon black will suppress the imagined mode.

When excited and driven under the TM mode, the electric field generated toward the pipe 11 is absorbed by the carbon black in the pipe 11, thereby becoming non-driven. When excited and driven under the TE mode, however, the influence of carbon black contained in the pipe 11 itself can be effectively eliminated. The needed resonance characteristic can be gained when the form of the antenna and the location of the excitation are further taken into consideration.

FIG. 10 shows a fourth embodiment of the present invention which is derived from considering the above-cited matters and in which the resonance chamber 133 is a cylindrical body having a diameter of 62 mm and a length of 113 mm. Exciting and transmitting linear antenna 25, and detecting and receiving linear antenna 26 are arranged inside the resonance chamber 133. Arranged around the outer circumference of the cylindrical resonance chamber 133 is a microwave circuit 27, from which a microwave signal is supplied to the antenna 25, while the microwave signal received by the antenna 26 is received by the microwave circuit 27, thereby achieving wave detection.

FIG. 11 shows a result of having measured the frequency characteristic of the device arranged according to the fourth embodiment of the present invention. The solid line shows the transmission power when the pipe 11, which is made of rubber, has no methanol flowing therethrough. A broken line shows transmission power in the case where the pipe 11 has methanol flowing therethrough. As apparent from the graph, it has been found that attenuation by methanol is largest at 5.3 GHz, when the change of attenuation reaches about 50%, and when the microwave driving frequency signal supplied from the generator 16 is set to 5.3 GHz.

Figure 12A:
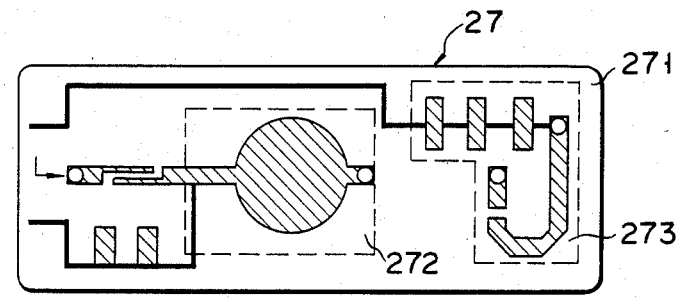
FIG. 12A is a plan view showing a microwave circuit section employed by the fourth embodiment.
Figure 12B:
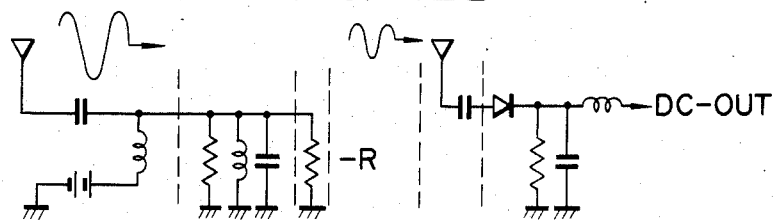
FIG. 12B is a circuit diagram showing the microwave circuit concretely.

FIG. 12A shows an arrangement of the microwave circuit 27 wherein an oscillating circuit 272, a wave detecting circuit 273 and a microwave circuit for the antenna line are formed on a sheet of substrate 271 of 32 mm×83 mm, for example, using distributed constant lines. Since line widths and lengths of the pattern have electrical significance, the circuit diagram of the microwave circuit 27 is shown in FIG. 12B.

Figure 13:
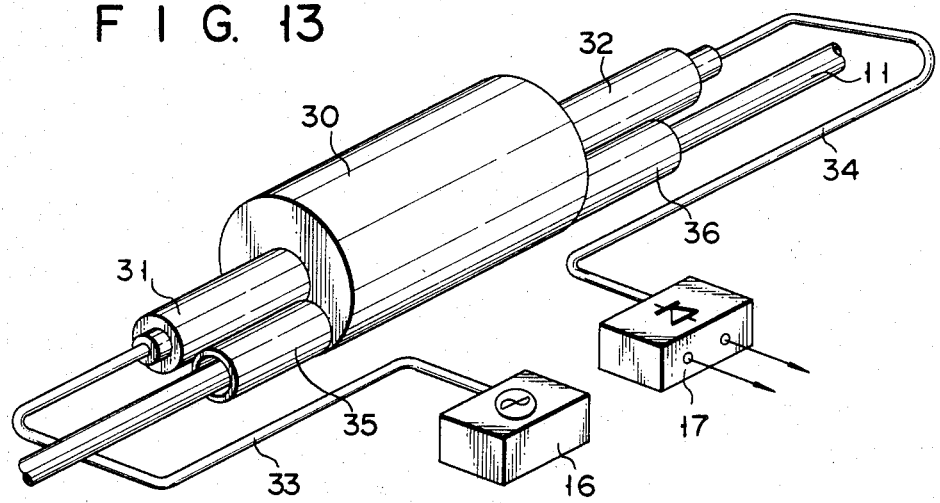
FIG. 13 shows the configuration of a fifth embodiment of the present invention.

FIGS. 13 and 14 shows a fifth embodiment of the present invention, in which the fuel pipe 11 made of a high frequency permeable material passes through one closed end of a cylindrical microwave wave guide 30, extends along the inner wall thereof, and then passes through the other closed end thereof. Impedance matching wave guides 31 and 32 are projected from both closed ends of the microwave wave guide 30, respectively, and at the central axis portion thereof. Coaxial cables 33 and 34 are connected to the wave guides 31 and 32, which are coaxial with the microwave wave guide 30 and smaller in diameter than the microwave wave guide 30. The coaxial cables 33 and 34 are also connected to the microwave generator 16 and the detector 17, respectively.

The coaxial cables 33 and 34 connected to the wave guides 31 and 32 are further extended into the wave guide 30 along the central axis portion thereof to form a coaxial wave guide.

Microwave leakage-preventing wave guides 35 and 36 are projected from both ends of the wave guide 30 through which the pipe 11 passes. The cut-off frequency for the wave guides 35 and 36 is set sufficiently higher than the microwave frequency used for measurement to thereby prevent any microwaves from leaking outside.

The impedance matching wave guides 31 and 32 are so-called λ/4 matching sections in which their lengths are set to be ¼ of the wavelength λ of the microwave used for measurement. Their characteristic impedances $Z_T$ are set to be:

$$Z_T = \sqrt{Z_c \cdot Z_g}$$

Zc represents the characteristic impedance of the coaxial cables 33 and 34, and Zg represents that of the wave guide 30.

In the case of the device according to the fifth embodiment of the present invention, the wave guide 30 and the coaxial cables 33 and 34 are matched in impedance by the wave guides 31 and 32, and microwaves are not reflected but transmitted effectively, when alcohol is almost entirely absent from the fuel. When alcohol is mixed in fuel, however, the dielectric constant ϵ, the dielectric loss tangent tan δ of the fuel increase and the characteristic impedance Zg of the wave guide 30 changes. Accordingly, the impedance-matched state of the wave guide 30 and coaxial cables 31 and 32 is cancelled and reflected waves are generated, thereby causing the transmitted microwave to be attenuated.

FIG. 15 shows an equivalent circuit for the fifth embodiment of the present invention, in which the resistance caused by dielectric loss tangent tan δ of the mixed fuel in the pipe 11 is represented by R.

What is claimed is:

1. A device for measuring the amount of alcohol in a mixed fuel, comprising:
   fuel pipe means for containing a flow of said mixed fuel, said fuel pipe means being microwave permeable and having a longitudinal axis;
   microwave chamber means for surrounding a portion of said fuel pipe means, said chamber means having first and second end faces substantially perpendicular to said pipe means longitudinal axis;
   microwave antenna means for transmitting a microwave signal into said microwave chamber means, and for receiving microwaves from said microwave chamber means;
   first and second metal extensions respectively coupled to said first and second end faces and extending in opposite directions along a line substantially parallel to said pipe means longitudinal axis, lengths of said first and second extensions being predetermined to cause a cut-off frequency in each of said extensions to be greater than a frequency of the transmitted microwave signal;
   microwave generator means for supplying said microwave signal to said antenna means; and
   microwave signal detecting means for receiving the microwaves received by said antenna means, and for providing an output signal corresponding to the received microwaves.

2. An apparatus according to claim 1, wherein said pipe means includes a rubber hose.

3. An apparatus according to claim 1, wherein said pipe means includes a material selected from the group comprising teflon and nylon.

4. An apparatus according to claim 1, wherein said microwave chamber means includes a pair of wave guides which are opposed to each other with said fuel pipe means interposed between them, to cause microwaves transmitted through one of the wave guides to be received by other wave guide, said microwaves permeating through the fuel pipe means.

5. An apparatus according to claim 4, wherein each of the paired wave guides includes an antenna section formed at an end of the corresponding wave guide opposite to the fuel pipe, the antenna sections being coupled to the microwave antenna means.

6. An apparatus according to claim 1, wherein said microwave chamber means is attached to the fuel pipe means, and includes an integrally attached cylindrical metal body, said cylindrical metal body being fixed to an outer circumference of said fuel pipe means.

7. An apparatus according to claim 1, wherein said fuel pipe means supplies said mixed fuel to an engine in which alcohol-mixed fuel is used.

8. An apparatus according to claim 1, wherein said microwave chamber means includes (a) a wave guide attached to one side of said fuel pipe means, and (b) a reflecting plate attached to the fuel pipe means on a side opposite said wave guide, said microwave antenna means being connected to said wave guide, said microwave antenna means receiving microwaves reflected by the reflecting plate.

9. An apparatus according to claim 8, wherein said microwave antenna means is connected to the microwave generator means and microwave detecting means through a circulator.

10. An apparatus according to claim 1, wherein said microwave chamber means includes a resonance chamber comprising a cylindrical body through which said fuel pipe means passes.

11. An apparatus according to claim 10, wherein said microwave chamber means includes a cylindrical metal resonance chamber through which said fuel pipe means passes coaxially.

12. An apparatus according to claim 11, wherein said fuel pipe means passes through said resonance chamber, and wherein said antenna means includes transmitting and receiving antennas disposed on opposite sides of said fuel pipe means.

13. An apparatus according to claim 12, wherein said transmitting antenna and said receiving antenna are arranged side by side.

14. An apparatus according to claim 10, wherein said fuel pipe means includes a rubber hose, and wherein said resonance chamber is driven in TE mode.

15. An apparatus according to claim 10, wherein said fuel pipe means passes through the cylindrical body along an inner circumference thereof.

16. An apparatus according to claim 15, further including first and second impedance matching wave guides projecting from both ends of the cylindrical body at a central axis portion thereof, and wherein said antenna means includes coaxial cables for supplying and receiving microwaves, said cables being connected to said impedance matching wave guides and connected to each other at the central axis portion of the cylindrical body to enable said resonance chamber to serve as a coaxial wave guide.

17. An apparatus according to claim 1, wherein the frequency of the transmitted microwave signal is substantially 5.3 GHz.

18. Apparatus according to claim 1 wherein said first and second metal extensions are integrally formed as a metal pipe having at least one opening adjacent said microwave antenna means.

19. Apparatus according to claim 1 wherein said microwave chamber means includes a metal cylindrical body, said metal extensions being coupled to end faces of said cylindrical body, and wherein said fuel pipe means extends through a length of said cylindrical body.

20. Apparatus for measuring the amount of alcohol in a mixed fuel passing through a microwave permeable fuel pipe having a longitudinal axis, comprising:

a microwave chamber adapted to be coupled to said fuel pipe and surrounding a portion of said fuel pipe so as not to penetrate to an interior of said fuel pipe, said chamber means having first and second end faces substantially perpendicular to said pipe longitudinal axis;

microwave antenna means coupled to said chamber, for transmitting a microwave signal into said chamber, and for receiving from said chamber microwaves which haves passed through said fuel pipe;

microwave generator means, for providing said microwave signal to said antenna means; and first and second metal extensions respectively coupled to said first and second end faces and extending in opposite directions along a line substantially parallel to said pipe longitudinal axis, lengths of said first and second extensions being predetermined to cause a cut-off frequency in each of said extensions to be greater than a frequency of the transmitted microwave signal;

microwave detector means for receiving the microwaves received by said antenna means, and for providing an output signal corresponding to said received microwaves.

* * * * *